US012708249B2

(12) United States Patent
Weber et al.

(10) Patent No.: US 12,708,249 B2
(45) Date of Patent: Aug. 18, 2026

(54) MEDICAL ENDOSCOPIC INSTRUMENT

(71) Applicant: Richard Wolf GmbH, Knittlingen (DE)

(72) Inventors: Bernd Claus Weber, Karlsruhe (DE); Moritz Tewes, Bretten (DE)

(73) Assignee: RICHARD WOLF GMBH, Knittlingen (DE)

( * ) Notice: Subject to any disclaimer, the term of this patent is extended or adjusted under 35 U.S.C. 154(b) by 498 days.

(21) Appl. No.: 17/908,096

(22) PCT Filed: Mar. 2, 2021

(86) PCT No.: PCT/DE2021/200028
§ 371 (c)(1),
(2) Date: Aug. 30, 2022

(87) PCT Pub. No.: WO2021/175386
PCT Pub. Date: Sep. 10, 2021

(65) Prior Publication Data
US 2023/0112879 A1 Apr. 13, 2023

(30) Foreign Application Priority Data
Mar. 3, 2020 (DE) ..................... 10 2020 202 686.6

(51) Int. Cl.
*A61B 1/00* (2006.01)
*A61B 1/04* (2006.01)
(Continued)

(52) U.S. Cl.
CPC ........ *A61B 1/00096* (2013.01); *A61B 1/0011* (2013.01); *A61B 1/043* (2013.01);
(Continued)

(58) Field of Classification Search
CPC . A61B 1/00096; A61B 1/0605; A61B 1/0646; A61B 1/0684; G02B 6/003;
(Continued)

(56) References Cited

U.S. PATENT DOCUMENTS 4,584,988 A * 4/1986 Nishioka .................. A61B 1/07 600/177
4,736,734 A * 4/1988 Matsuura ................. G02B 7/10 600/110
(Continued)

FOREIGN PATENT DOCUMENTS

DE 102018202243 A1 8/2019
JP 2000070214 A * 3/2000 ............. A61B 1/121
(Continued)

OTHER PUBLICATIONS

Kotz, F. [et. al.]: Three-dimensional printing of transparent fused silica glass. In: Nature, vol. 544, 2017, S. 337-342.—DOI: 10.1038/nature22061—ISSN 0028-0836.
(Continued)

*Primary Examiner* — Michael J Carey
*Assistant Examiner* — Stephen Floyd London
(74) *Attorney, Agent, or Firm* — McGlew and Tuttle, P.C.

(57) ABSTRACT

A medical endoscopic instrument includes a distal elongated insertion section (1) for minimally invasive insertion into a human or animal body, with at least one LED (5) arranged in a distal end section of the insertion section (1), and a lens system (19) arranged distally of the LED (5) with an optical axis (x). The lens system (19) includes a first lens (29) and a second lens (31) arranged distally of the first lens (29). The second lens (31) has a proximally extending sleeve extension (35). The sleeve extension (35) has a first reference surface for positioning the second lens (31) in relation to the insertion section (1) and a second reference surface (39) for positioning the first lens (29) in relation to the second lens (31).

24 Claims, 4 Drawing Sheets

(51) Int. Cl.
*A61B 1/06* (2006.01)
*B33Y 80/00* (2015.01)

(52) U.S. Cl.
CPC .......... *A61B 1/0646* (2013.01); *A61B 1/0684* (2013.01); *B33Y 80/00* (2014.12)

(58) Field of Classification Search
CPC ...... G02B 7/021; G02B 9/10; G02B 23/2461; G02B 23/2469; G02B 13/18
See application file for complete search history.

(56) References Cited

U.S. PATENT DOCUMENTS

| | | | | | |
|---|---|---|---|---|---|
| 4,838,246 | A * | 6/1989 | Hahn | A61B 18/26 | 600/128 |
| 5,596,666 | A * | 1/1997 | Miyano | A61B 1/00096 | 385/118 |
| 6,110,106 | A | 8/2000 | Mackinnon et al. | | |
| 8,169,470 | B2 | 5/2012 | Ishihara et al. | | |
| 2002/0048172 | A1* | 4/2002 | Wada | G02B 9/10 | 362/268 |
| 2004/0188689 | A1* | 9/2004 | Shono | H10H 20/8316 | 257/E33.073 |
| 2007/0046778 | A1* | 3/2007 | Ishihara | A61B 1/0638 | 348/68 |
| 2010/0085466 | A1* | 4/2010 | Fujimori | G02B 13/0035 | 348/340 |
| 2011/0001061 | A1 | 1/2011 | Ishihara et al. | | |
| 2012/0253129 | A1* | 10/2012 | Kitano | A61B 1/07 | 600/165 |
| 2014/0254034 | A1 | 9/2014 | Lyu | | |
| 2014/0296638 | A1* | 10/2014 | Komukai | A61B 1/00096 | 600/121 |
| 2014/0346332 | A1* | 11/2014 | Honda | A61B 1/0625 | 250/227.21 |
| 2015/0038787 | A1* | 2/2015 | Nishimura | A61B 1/0638 | 600/109 |
| 2015/0257630 | A1* | 9/2015 | Sone | A61B 1/00 | 600/168 |
| 2016/0106306 | A1* | 4/2016 | Furuta | G02B 23/2461 | 600/176 |
| 2016/0170166 | A1 | 6/2016 | Alasirniö et al. | | |
| 2017/0105258 | A1 | 4/2017 | Sakai et al. | | |

FOREIGN PATENT DOCUMENTS

| | | | | |
|---|---|---|---|---|
| JP | 4391772 | B2 | 12/2009 | |
| WO | 9517845 | A1 | 7/1995 | |
| WO | 2013092740 | A1 | 6/2013 | |
| WO | WO-2019028458 | A1 * | 2/2019 | A61B 1/00096 |

OTHER PUBLICATIONS

Verband Deutscher Glasblaser: Laserbasierte Technologien. In: VDG-Nachrichten, vol. 3, 2016, S. 6-10.
Kretschmer Simon et al. "Integration and bio-compatible packaging of multi-modal endoscopic imagers using 3D glass micro structuring" Proceedings of spie; [proceedings of spie issn 0277-786x vol. 10524], Spie, US, vol. 10545, Feb. 22, 2018 (Feb. 22, 2018), pp. 105450q-105450q, Doi: 10.1117/12.2289480, ISBN: 978-1-5106-1533-5. Xp060105698.

* cited by examiner

H
31
25
29
5
19

H
31
25
19
29
5

H
31
25
29
5
19

19
31
25
29
5
15
11a 19
39
31
25
29
5
15
11a
35
37
33

MEDICAL ENDOSCOPIC INSTRUMENT

CROSS REFERENCE TO RELATED APPLICATIONS

This application is a United States National Phase Application of International Application PCT/DE2021/200028, filed Mar. 2, 2021, and claims the benefit of priority under 35 U.S.C. § 119 of German Application 10 2020 202 686.6, filed Mar. 3, 2020, the entire contents of which are incorporated herein by reference.

TECHNICAL FIELD

The present disclosure relates to a medical endoscopic instrument with a distal elongated insertion section for minimally invasive insertion into a human or animal body.

BACKGROUND

Using endoscopes to make video recordings of the interior of a human or animal body for the purposes of medical diagnosis and/or therapy is known. In doing so it is usual to illuminate the interior of the body with a light source and to carry out imaging by means of an image sensor, for example a CCD (charge-coupled device) or CMOS (complementary metal oxide semiconductor) sensor. As the spectral sensitivity of such an image sensor generally differs from that of the human eye, in the prior art a correction filter is usually placed in the image path before the image sensor in order to produce a natural colour impression of the taken image. Especially in the red and infrared wavelength range, the typically used image sensors are usually more sensitive than the eye, so that the correction filters used in this wavelength range have a particularly strongly dimming effect. However, a drawback of this is that due to the correction filter, significant portions of the light output that is coupled into the interior of the body and converted into heat there, are not used for image taking by the image sensor.

For better utilisation or saving of the coupled-in light output, WO 95/17845 proposes not placing a dichroitic correction filter in the image path in front of the CCD sensor, but arranging it in front of an external light source or in a light guiding system of the endoscope. Therefore, light that the CCD sensor is not to record, is not coupled into the body in the first place. In this way, the tissue is protected against the coupling in of unnecessary light output and thereby heat generated in the tissue.

However, the endoscopic video system known from WO 95/17845 is not suitable to be optionally used for white light endoscopy and for fluorescence endoscopy. In contrast to white light endoscopy, in fluorescence endoscopy, which is used, for example, for the detection and localisation of pre- and early malignant tissue, it is not a matter of natural real-colour depiction of the tissue, but of fluorescence stimulation with which pathological tissue can be distinguished from healthy tissue. In doing so, the pathological tissue stimulated by means of light radiation can itself, or an accumulation of bacteria indicating pathological tissue, can specifically fluoresce and thus be identifiably localized with regard to the surrounding healthy tissue. Fluorescence endoscopy can, for example, be performed as part of photodynamic diagnosis (PDD) and/or photodynamic therapy (PDT) by way of a photosensitiser or marker agent which selectively accumulates on pathological material. Alternatively, endogenic fluorescence (autofluorescence) of the pathological tissue can also be made visible without the use of a photosensitiser or marker agent.

Described in DE 10 2018 202 243 A1 is a medical endoscopic instrument, which can optionally be used for fluorescence endoscopy and for white light endoscopy and nevertheless protects the tissue against the coupling in of unusable light output in that it better utilizes the coupled-in light output for the respective purpose of use. In doing so, a light filter is inserted before the white light LED.

However, it is problematical that the luminous spectrum of the blue light LED intended for fluorescence endoscopy still has, for example, relatively large portions in a wavelength range of 440 to 470 mm, which muffle the relatively weak fluorescence signal of the photosensitiser or marker agent. Although in blue light operation, a longpass filter arranged before the image sensor, for example with a spectral edge at approximately 470 nm, would improve the signal-noise ratio for fluorescence endoscopy, in white light operation it would undesirably block blue and violet light portions up to approximately 470 nm in the visible spectrum which would lead to colour distortions. Accordingly, in principle, a shortpass filter with a spectral edge at approximately 440 nm arranged before the blue light LED makes more sense, but at the same time this reduces the amount of light emerging from the illumination path, which must be as great as possible for effective fluorescence stimulation. Although, in principle, a lens system arranged distally before the blue light LED allows the light output to be increased, with its axial length the lens system takes up installation space by which the blue light LED has to be set back proximally. This in turn increases an unwanted keyhole effect. If, in order to reduce the axial length of the lens system, the axial thickness of the lenses of the lens system is made very small, the precise and stabile positioning and fixing of the lenses relative to each other and in relation to the instrument becomes very difficult and laborious.

SUMMARY

It is therefore the objective of the present disclosure to provide a medical endoscopic instrument with an efficient lens system distally of an LED, wherein on the one hand the lens system allows as distal a position of an LED as possible, and on the other hand the lenses of the lens system can be positioned and fixed as simply, precisely and as stably as possible.

According to one aspect of the present disclosure, a medical endoscopic instrument is provided with a distal elongated insertion section for minimally invasive insertion into a human or animal body, with at least one LED arranged in a distal end section of the insertion section, and a lens system arranged distally of the LED with an optical axis, wherein the lens system comprises a first lens and a second lens arranged distally of the first lens. The second lens has a proximally extending sleeve extension, wherein the sleeve extension has a first reference surface for positioning the second lens in relation to the insertion section and a second reference surface for positioning the first lens relation to the second lens.

The sleeve extension of the second lens has the effect of, on the one hand reducing the installation costs of the lens system, and, on the other hand, of guaranteeing precise and stable alignment of the lenses in relation to the optical axis. As the dimensions of the optically active area of the lenses, i.e. without the sleeve extension as a mechanically active area, are very small in the lateral direction and, above all, in the axial direction, without the sleeve extension the precise positioning and fixing of the lenses in relation to the optical axis would be a very demanding manual process if adequate quality in terms of alignment and fixation is to be achieved. The sleeve extension facilitates alignment in relation to the optical axis and fixation enormously, which considerably reduces the installation cost of the lens system. This is because, preferably on the outside, the sleeve extension forms the first reference surface which in the instrument only allows unequivocal alignment in relation to the instrument axis. For example, the sleeve extension can be perfectly fitted into an inner diameter of a mounting in the instrument. The outer first reference surface on the sleeve extension, for example in the form of an external cylinder surface can be very simply and stably attached by adhesion in a mounting in the instrument. This is, in particular, very stable and durable. Furthermore, in this way a tight connection can be created so that no fluids can penetrate laterally past the lens system and into the instrument. However, in the circumferential direction, the sleeve extension does not have to be enclosed all round or be a closed cylindrical surface, but can have circumferentially distributed, lateral reference surfaces, which allow unequivocal alignment and fixation in relation to the instrument axis. If the sleeve extension does not have a circumferentially closed first reference surface in the form of a cylinder surface, but comprises $n \geq 3$ circumferentially distributed, lateral first reference surfaces, these are preferably distributed in an n-fold rotationally symmetrical manner in relation to the optical axis.

With the second reference surface, which can preferably be an axially orientated annular surface, against which the first lens is supported, a defined position of the first lens relative to the second lens, preferably in the axial position, is enabled. Alternatively, or additionally, a radial inner surface of the sleeve extension can form the second reference surface or a third reference surface, wherein the inner surface determines the positioning of the first lens relative to the second lens, preferably in the axial, radial and/or rotational direction. A defined relative position in the rotational direction plays a role if the lens system is not rotationally symmetrical in relation to the optical axis. The inner surface can extend conically in order to achieve a relative position both in the axial and radial direction. However, preferably the first reference surface indirectly, and the second reference surface directly, determine the position of the first lens relative to the second dimension in one direction respectively, e.g. axially and radially. For this, the normal of the first and the second references surface preferably have vector components that are orientated orthogonally with regard to each other. The first reference surface can indirectly determine the relative position of the first lens to the second lens, at least in one dimension, in that the first lens preferably has a reference surface for positioning the first lens relative to the insertion section.

Optionally, the sleeve extension of the first lens and/or the sleeve extension of the second lens can, on its surface facing the mounting in the instrument, be provided with a radially surrounding or just sequentially configured recess. Corresponding to this, i.e. arranged at the matching and defined height, on its inner side the mounting in the instrument can have a radially surrounding or sequential protrusion, for example in the form of a latch. Alternatively, or additionally, inversely the radial protrusion can be located on one of the sleeve extensions, and the complementary radial recess on the mounting in the instrument. This allows a defined axial positioning of the corresponding lens with its sleeve extension opposite the mounting in the instrument and also ensures a positive connection. If the flexibility of the sleeve extension and/or mounting is not great enough for an engagement procedure, the sleeve extension and the mounting can each be provided with a radial recess applied at axial positions complementing each other, and engagement and the desired positive connection can be achieved with an additional flexible O ring (made of silicone, for example), which fills the resulting intermediate space between the sleeve extension and mounting at location of the recess. On the basis of its flexibility, the O ring can provide the necessary pliability during installation and/or still before engagement. Circumferential sealing can also be supported by such an O ring.

The arrangement of the lens system, preferably in the form of a "converging lens-light filter-diverging lens" arrangement, distally of the LED increases the light output to a considerable extent, wherein the light filter in particular can ensure a good signal-to-noise ratio in fluorescence endoscopy. The arrangement of a "converging lens-light filter-diverging lens" lens system distally of the LED is so efficient because the converging lens initially gathers in the light emitted from the LED in the form of a Lambertian radiator and bundles it towards the light filter so that the angle of incidence on the light filter is as small as possible. With an increasing angle of incidence, in the case of a shortpass filter for example, the transmission spectrum can be strongly displaced to the shortwave spectrum. This is the case, for example, if the shortpass filter is a dichroitic filter, i.e. an optical filter based on thin interference layers. The light output can therefore sharply decrease with the angle of incidence. As the converging lens minimizes the angle of incidence, the light output is increased accordingly. In order not to only achieve spot-like but also area illumination of the tissue, the diverging lens arranged in the illumination path after the light filter widens out the light cone again.

"Light spectrum" here means an intensity distribution$I(\lambda)$ of the light as a function of the wavelength $\lambda$, of the light. The mean intensity in a wavelength range between a wavelength $\lambda_1$ and wavelength $\lambda_2$ is defined here as $$\bar{I} = \int_{\lambda_1}^{\lambda_2} \frac{I(\lambda)}{\lambda_2 - \lambda_1} d\lambda.$$

"Transmission spectrum" here means a distribution of the percentage light transmission$T(\lambda)$ as a function of the wavelength $\lambda$ of the light. The mean transmission in a wavelength range between a wavelength $\lambda_1$ and wavelength $\lambda_2$ is defined here as $$\bar{T} = \int_{\lambda_1}^{\lambda_2} \frac{T(\lambda)}{\lambda_2 - \lambda_1} d\lambda.$$

If the functions$I(\lambda)$ and/or $T(\lambda)$ for certain wavelengths or spectral lines in the first and/or second wavelength range are not locally integrable, such wavelengths or spectral does should be ignored in the averaging. The luminous spectrum of the LED suitable for fluorescence endoscopy can, for example, have a relative sharp peak at 405 nm to 410 nm with a half-width of approximately 20 nm. The LED would then be a blue light LED. The luminous spectrum suitable for white light endoscopy of a second LED arranged in parallel to the first LED can correspond to a typical light spectrum of a white light LED between 410 nm and 710 nm.

The at least one LED is arranged as the light source in the insertion section in order to generate light "in situ" in the body, so that no external light source and no light guide system are required. With a first LED, fluorescence endoscopy can be performed and white light endoscopy with a second LED. Optionally, switching can take place between performing fluorescence endoscopy with the first LED and performing white light endoscopy with the second LED. An image sensor, for example a CCD sensor or CMOS sensor can accordingly be optionally used for fluorescence endoscopy and white light endoscopy, and requires no correction filter in the form of a shortpass filter in the image path, which would considerably reduce the light output usable for imaging in white light operation. With the instrument disclosed here, fluorescence endoscopy can be performed as part of a PDD and/or PDT. Preferred forms of embodiment of the instrument can, however, be mainly configured for PDD, if, for example, the first LED has a shortwave, blue first luminous spectrum for efficiently inducing fluorescence.

Optionally, the sleeve extension of the second lens can be a one-piece, integral part of the second lens. Correspondingly, the sleeve extension of the first lens can be a one-piece, integral part of the first lens. In other words, the respective lens forms a proximally open "pot", the distal "base" of which is optically effective and the external wall of which is mechanically effective for alignment, fixation and lateral sealing. In this way a separate fitting is avoided, into which the individual components of the lens system would have to be laboriously fitted.

Optionally, the sleeve extension can extend longer by a factor of 2 or more in the axial direction than the axial thickness of the second lens on the optical axis. More particularly a factor of 5 or more can be advantageous here. The longer the sleeve extension extends in the axial direction, the more firmly and precisely the lens system can be arranged and fixed in the instrument. The sleeve extension can even extend longer by a factor of 2 or more in the axial direction than the diameter of the respective lens. The structural integrity and brittleness of the lens form the upper limit for the axial length of the respective sleeve extension, if it is very long. Furthermore, the axial length is limited for production reasons.

Optionally, the sleeve extension of the second lens can surround the first lens, at least in sections. Preferably, in doing so the sleeve extension of the first lens forms a distally acting abutment against which a proximal end of the sleeve extension of the second lens is supported. A first distal section of the sleeve extension of the first lens preferably has a smaller outer diameter than a second proximal section of the first lens. The outer diameter of the first distal section of the sleeve extension of the first lens preferably fits into the inner diameter of the sleeve extension of the second lens. The outer diameter of the second distal section of the sleeve extension of the first lens preferably corresponds with the outer diameter of the sleeve extension of the second lens. The distally acting abutment of the first lens is preferable formed by a circumferential ledge between the first and second section of the sleeve extension of the first lens.

Optionally, the first lens can form a distally acting abutment which is axially supported against the second reference surface of the sleeve extension of the second lens. The abutment is advantageous in order to achieve precise axial positioning and fixation of the components of the lens system with regard to each other.

Optionally, the LED can be circumferentially surrounded by the sleeve extension of the first lens. The LED can thus be arranged as close as possible to a preferably proximal planar side of the optically effective part of the first lens in order to minimize losses.

Optionally, the sleeve extension can be produced by removing a core of a blank by means of an ablative process, for example selective laser etching (SLE). For example, with an SLE process, components can be produced from sapphire and glass. The core of the blank can be ablated using a micro-scanner and a precise axis system with an accuracy of 1 micrometre. The thus produced surfaces can have a mean surface roughness $R_z$ of less than 1 micrometre.

Optionally, the sleeve extension of the converging lens and/or the diverging lens can be produced by means of a combined additive and ablative process. For example, in a first step, nanoparticles of ultrapure quartz glass can be mixed with a small quantity of liquid plastic and, by means of stereolithography, hardened by way of light at certain points. In a second step, the material that remains liquid is then washed out in a solvent bath so that only the desired, hardened structure is left. The plastic still mixed into this glass structure can then be removed through heating. In a final sintering process, the glass can then be heated to such an extent that the glass particles melt and fuse together.

Optionally, the sleeve extension of the converging lens process and/or the diverging lens can be produced by means of a purely additive process. Here, the glass can be applied in layers with an oven that acts as a melting and extrusion unit. For smoothing the surfaces, a plasma burner can be used.

Optionally, the first lens can be a converging lens and the second lens a diverging lens. In this way, by way of the lens system, undesirable keyhole effects can be reduced.

Optionally, a light filter can be arranged between the first lens and the second lens. The lens system is preferably a "converging lens-light filter-diverging lens" arrangement.

Optionally, circumferentially the light filter can be surrounded by the sleeve extension of the second lens. The light filter can thus be arranged as close as possible to a preferably proximal planar surface of the optically effective part of the second lens, in the form of a diverging lens, for example, in order to minimize losses.

Optionally the light filter can be a shortpass filter. For example, in fluorescence operation, the shortpass filter can have a spectral edge at approximately 440 nm in order to allow through shorter wavelengths with a mean transmission of over 90% and to block higher wavelengths with a mean transmission of under 10%. A longpass filter in the image path distally of the image sensor can be configured so that its spectral edge is also at approximately 440 nm, so that medium and long wave portions of the blue light are allowed to pass in white light operation in order to ensure good colour reproduction in the white light range.

Optionally, the first lens can be a plano-convex lens and/or the second lens a plano-concave lens, wherein the respective planar surface faces in the proximal direction. This is particularly useful in order to minimize the axial length of the lens system and its axial distance from the LED over a large area and not just at points so as to capture as many LED rays as possible in the first and/or second lens. This is because, in order to reduce an undesirable keyhole effect, which impairs the efficiency fluorescence endoscopy, the LED should be arranged as far to distal as possible and the surface of the first lens facing the LED should have a minimum distance from the LED over a large area and not just at points. The more compact the lens system and the shorter its distance from the LED, or the greater its area at minimum distance from the LED, the more to distal the LED can be arranged and the greater the portion of the light rays emitted from the LED that reaches the entry surface of the first lens and is refracted towards the optical axis and can then also reach the light filter and the second lens in order to minimize an undesired keyhole effect.

Optionally, the first lens and/or the second lens can be a Fresnel lens. The axial length of the lens system is thus shortened further, as the axial "thickness" of the first and/or second lens is reduced.

Optionally, a first LED for fluorescence operation, a second LED for white light operation and an image sensor can be arranged on a common wall of the insertion section. Preferably this is a distal face side of the insertion section, wherein the first LED, the second LED and the image sensor are arranged to distal in the longitudinal direction of the insertion section. In this form of embodiment in particular, the lateral installation space for placing the first LED, the second LED and the image sensor on the face side is very limited. Available in the wall of the insertion section there may only be recesses available with a diameter of 1 mm or less per LED or image sensor. In extreme cases, the available diameter can even just be 0.5 mm.

Optionally, in a plane perpendicular to the line if sight, the image sensor can essentially be at the same distance from the first LED as from the second LED, and preferably be arranged between the first LED and the second LED. As result of this, a user can simply switch between either white light endoscopy and fluorescence endoscopy without the lighting angle and/or lighting intensity or shadowing in the image changing greatly. Although through controlling the first LED and the second LED differently, varying distances could possibly be compensated for, this would less efficient in term of energy. Preferably the image sensor is arranged centrally on the face side. The first and second LED can be arranged offset laterally therefrom with as small and equal lateral distance as possible on the face side.

Optionally, the lens system can be arranged distally from the first LED in a recess in a wall of the insertion section, wherein the wall defines an outer surface and the distance of a light emitting side of the first LED from the outer surface is at most two thirds of the diameter of the recess. The outer surface can preferably be an end face of the insertion section. The recess in the first LED causes a certain "tunnel vision" or keyhole effect, as due to the upstream lens system, the first LED is arranged proximally with regard to the outer surface.

Optionally, at least one protective element permeable for blue light can be arranged distally of the second lens. The at least one protective element can be a protective glass, protective plastic that is as thin as possible and/or a silicon dioxide layer applied distally to the second lens. The protective element can protect the second lens from mechanical damage, such as scratches and chemical damage such as through aggressive bodily fluids, cleaning or treatment media and/or oxidation.

Optionally the second lens, preferably configured as a diverging lens, can be made of a hard or scratch-proof and chemically resistant material, for example sapphire. The protection element can then be dispensed with. In this way the keyhole effect can be reduced further.

Optionally, in a plane perpendicular to the optical axis, a plurality of $n \geq 2$ first LEDs and/or a plurality of $m \geq 2$ second LEDs can be arranged in an n-fold or m-fold rotationally symmetrical manner with regard to a line of sight axis of the image sensor in the insertion section. In this way, undesirable shadowing is reduced both for white light endoscopy and for fluorescence endoscopy. In doing, the same number of first LEDs and second LEDs, i.e. n=m, can be provided, which are circularly arranged around the image sensor so that first LEDs and second LEDs alternate circumferentially. If the first LEDs are used as relatively dim blue LEDs for fluorescence endoscopy, it can, however, be advantageous to provide more first LEDs than second white LEDs, i.e m>n.

According to a second aspect of the present disclosure, a method is provided for producing a lens system, which is suitable for use in a distal end of a medical endoscopic instrument and comprises at least one lens, wherein a sleeve extension of the lens is created by removing a core of a blank by means of an ablative process, for example selective laser etching (SLE). For example, with an SLE process, components can be produced from sapphire and glass. The core of the blank can be ablated using a micro-scanner and a precise axis system with an accuracy of 1 micrometre. The thus produced surfaces can acquire a mean surface roughness $R_z$ of less than 1 micrometre.

Optionally, through removal of the core of a blank, the at least one lens can acquire a pot-shaped form which has an optically effective pot base and a mechanically effective circumferential pot wall.

Optionally, an inner surface of the pot base can be ablated in a planar manner. The LED and/or light filter can be arranged on the planar, preferably proximally facing surface of the optically effective area, either directly or at a slight axial distance. Optionally, a light filter can also be attached to the inner surface of the pot base.

An outer surface of the pot base can optionally be arched. For example, the first lens can be ground as a plano-convex converging lens and the second lens as a plano-concave diverging lens.

Optionally, a sleeve extension of a further lens of a lens system can also be produced by removing a core of a blank by means of an ablative process, for example selective laser etching (SLE).

Optionally, the lenses can be arranged coaxially with regard to each other and at least partially in the axial direction fastened to each other in an interlocking manner as a pre-assembled lens system, and the pre-assembled lens system can be fitted into a distal end of a medical endoscopic instrument. The components of the lens system are preferably adhered to each other as a pre-assembled unit.

Optionally, the sleeve extension of the converging lens and/or the diverging lens or the respective entire component, consisting of a sleeve extension and the actual lens, can be produced by means of a combined additive and ablative process. For example, in a preliminary first, additive, step, nanoparticles of ultrapure quartz glass can be mixed with a small quantity of liquid plastic and, by means of stereolithography, hardened by way of light at certain or desired points. In a following, second step, the core of the blank is the form of material remaining liquid, is washed out in a solvent bath so that only the desired, hardened structure is left. The plastic still mixed into this glass structure can then be removed through heating. In a final sintering process, the glass can then be heated to such an extent that the glass particles melt and fuse together.

Optionally, the sleeve extension of the converging lens process and/or the diverging lens can be produced by means of a purely additive process. Here, the glass can be applied in layers with an oven that acts as a melting and extrusion unit. For smoothing the surfaces, a plasma burner can be used.

The disclosure is explained in more detail below by way of an example of embodiment shown in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
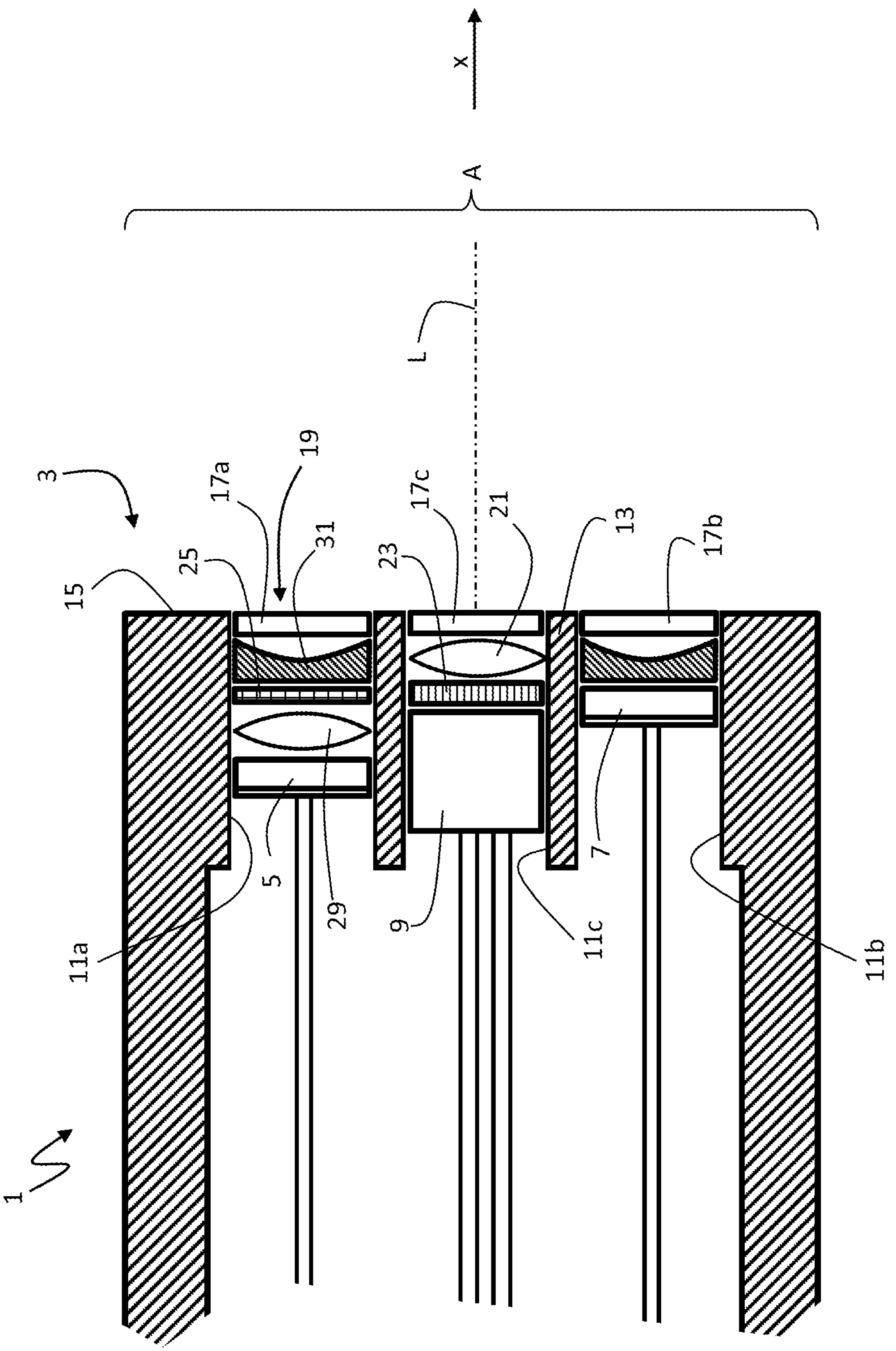
FIG. 1 is a schematic longitudinal sectional view through a distal section of an insertion section according to an example of embodiment of the medical endoscopic instrument disclosed herein.

Referring to the drawings, FIG. 1 shows a distal end section of an insertion section 1 of a medical endoscopic instrument. The insertion section 1 is intended for minimally invasive insertion into a human or animal body in order to be able to illuminate this with light and to make video or image transmission from inside the body possible. To ensure that insertion is minimally invasive, the outer diameter A of the insertion section 1 is as small as possible, and in this example of embodiment is less than 5 mm.

Arranged next to each other at a distal end face 3 of the insertion section 1 are a first LED 5, a second LED 7 and an image sensor 9, which are distally orientated in a common line of sight x, which in this example of embodiment corresponds to the longitudinal direction of the insertion section 1. The first LED 5, the second LED 7 and the image sensor 9 are each arranged in a recess 11*a,b,c* in a face wall 13 of the insertion section 1. The face wall 13 defines an outer surface 15 on the face side 3 of the insertion section 1. The first LED 5, the second LED 7 and the image sensor 9 are each arranged behind protective elements 17*a,b,c* in the form of thin protective glass panes which are each flush with the outer surface 15 on the face side 3 of the insertion section 1 and protect against mechanical damage, such as scratches and chemical damage such as through aggressive bodily fluids, cleaning or treatment media and/or oxidation. The protective elements 17*a,b,c* can also be configured as a common protective glass pane covering the first LED 5, the second LED 7 and the image sensor 9. The protective elements 17*a,b,c* are permeable for white light, and in this example of embodiment have a refractive index of at least 1.75 as well as a higher breaking strength and hardness than conventional optical glass. The protection elements 17*a,b,c* can be made of a synthetic monocrystalline crystal. However, the protective elements 17*a,b,c* are optional here as the proximally arranged optical elements can themselves be sufficiently resistant or can have a correspondingly resistant protective layer on the distal side.

The first LED 5 has a first luminous spectrum suitable for fluorescence endoscopy that here has a peak between 405 nm and 410 nm with a half value width of 20 nm in the be blue wavelength range. With this blue light of the first LED 5, as part of photodynamic diagnosis (PDD) and/or photodynamic therapy (PDT), a photosensitiser that selectively accumulates on pathological tissue can be made to fluoresce in the red wavelength range. Such fluorescing in the red wavelength ranges can be easily be recorded by the image sensor 9 with no shortpass filter arranged distally upstream. Distally upstream of the image sensor 9 are an objective lens 21 and a longpass filter 23 with a spectral edge at approximately 440 nm. The longpass filter 23 directly blocks shortwave blue light of the first LED 5 that is scattered back by the body, but in white light operation with the second LED 7 allows sufficient blue light portions through for good colour reproduction. However, the first luminous spectrum of the first LED 5 has significant portions above 440 nm, the direct reflection of which on the object to be observed, for example on human tissue, deadens the fluorescence image. As the spectral edge of the longpass filter 23 can be displaced further into the longwave range without impairing colouration in white light operation, a shortpass filter 25 with a spectral edge at approximately 440 nm is arranged upstream of the first LED 5.

The second LED 7 has luminous spectrum suitable for white light endoscopy, which here has a peak in a first wavelength range of 400 nm to 500 nm and in a second wavelength range of 550 nm to 700 nm decreases with increasing wavelength. The first LED 5 can have the same luminous spectrum as the second LED 7 if the fluorescence stimulation required for the envisaged fluorescence endoscopy can be brought about with it. In this case, the first LED 5 and the second LED 7 can be of the same type.

Figure 2B:
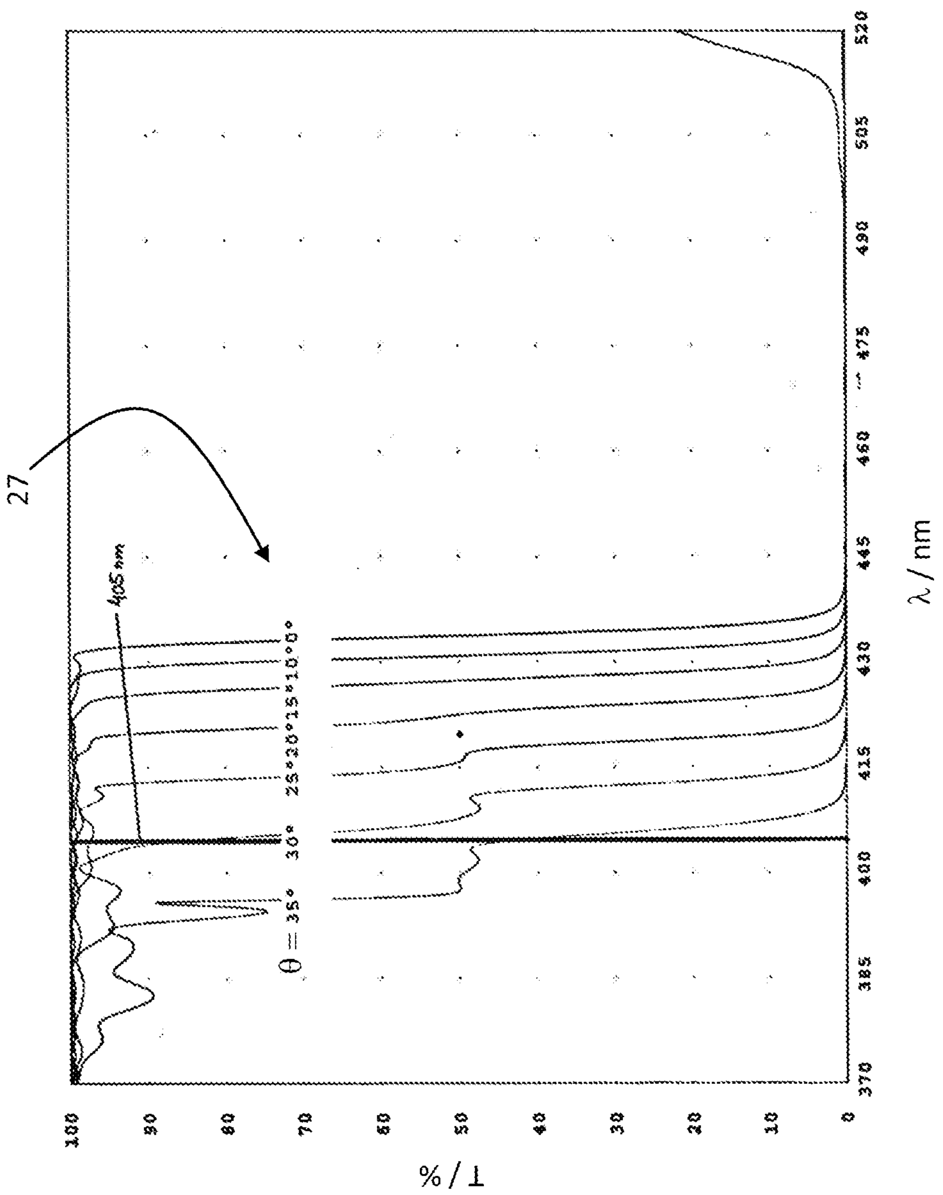
FIG. 2*b* is a graph showing a transmission spectrum of a light filter as a function of the angle of incidence onto the light filter.
Figure 2A:
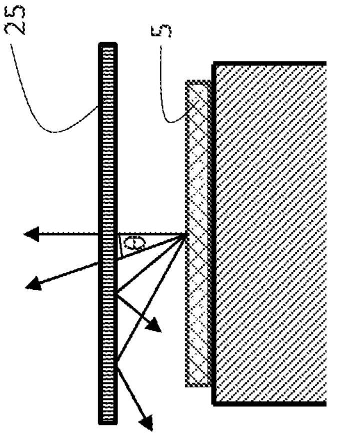
FIG. 2*a* is a schematic longitudinal sectional view to illustrate the principal radiation characteristics of an LED onto a light filter.
Figure 2C:
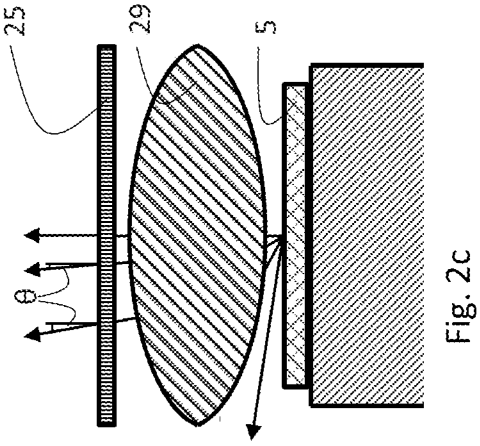
FIG. 2*c* is a longitudinal sectional view to illustrate the change in the beam compared to FIG. 2*a* when a converging lens is positioned between the LED and light filter.

In this example of embodiment, the second LED 7 is arranged offset distally with regard to the first LED 5. This is because a lens system 19 is arranged in front of the first LED 5 and behind the protective element 17*a*. The lens system 19 comprises a shortpass filter 25 with a spectral edge at approximately 440 nm. On average, in accordance with the transmission spectrum 27 (see FIG. 2*b*, where T indicates the transmission in percent), in a longwave wavelength range above the spectral edge, the light of the first LED 5 is transmitted less than in a shortwave wavelength range below the spectral edge. However, as seen in FIG. 2*b*, the length of the spectral edge of the shortpass filter 25 depends on the angle of incidence q (see FIG. 2*a*). As the first LED 5 emits lights like a Lambertian radiator and therefore large portions of light would reach the shortpass filter 25 at a high angle of incidence q and these portions of light would only be able to pass the shortpass filter 25 with very high losses, the lens system 19 comprises a first lens 29 in the form of a converging lens which is arranged between the first LED 5 and the shortpass filter 25. As can be seen in FIG. 2*c*, the converging lens 29 reduces the mean angle of incidence q significantly so that consequently the light output for the fluorescence light is significantly increased.

Figures 3A, 3B, 3C, 3D, 3E:
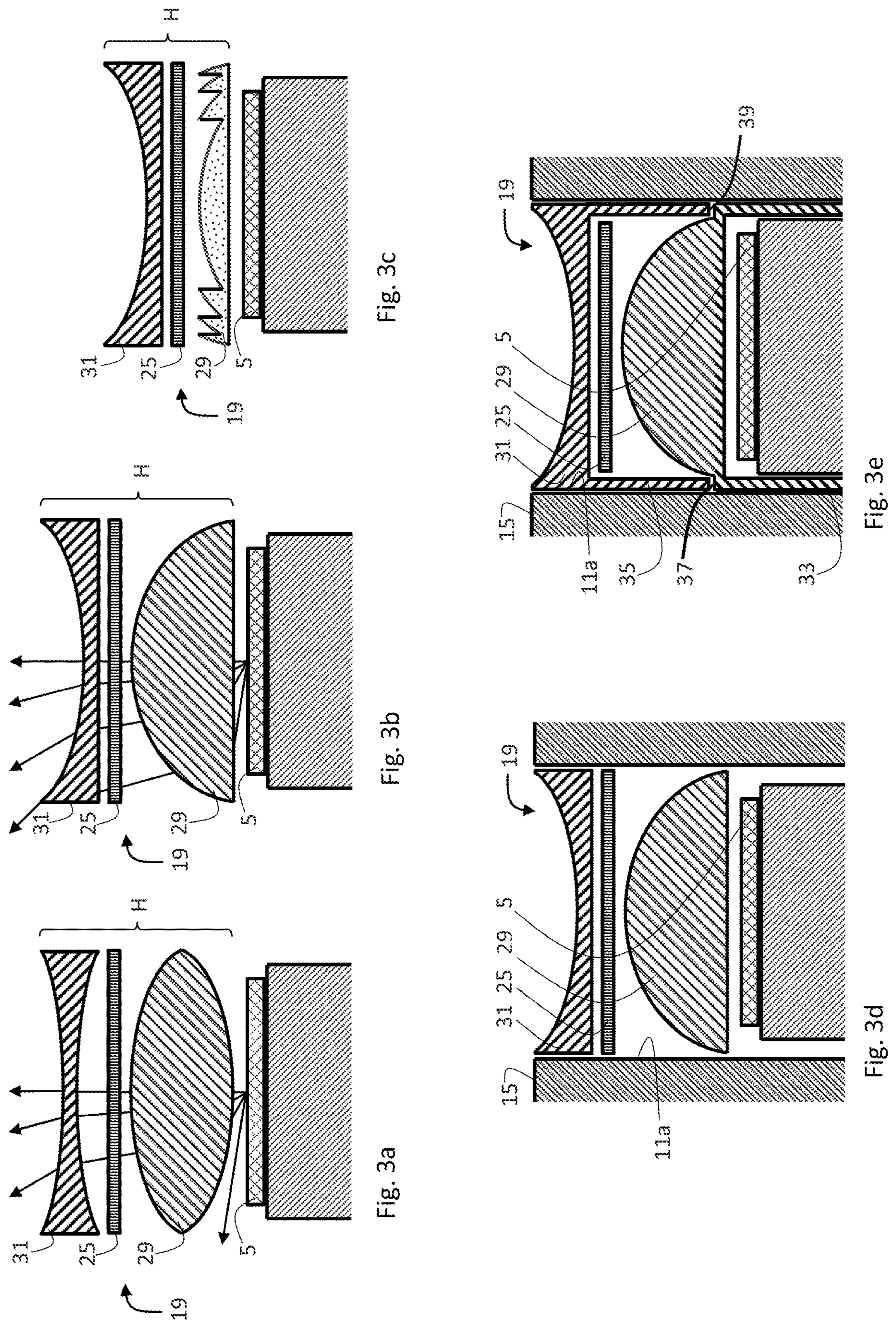
FIG. 3*a*, FIG. 3*b*, and FIG. 3*c* are schematic longitudinal sectional views of an optical arrangement of LED and light filter with a lens system in accordance with various examples of embodiments of the medical endoscopic instrument disclosed herein.
FIG. 3*d*, FIG. 3*e* and FIG. 3*f* are schematic longitudinal sectional views through a distal section of an insertion section according to examples of embodiments of the medical endoscopic instrument disclosed herein.

Due to the proximally set back position of the first LED 5 in comparison with the second LED 7, an unwanted keyhole effect is countered in that the lens system 19 comprises a second lens 31 in the form of a diverging lens, which is arranged distally of the shortpass filter 25. As shown in FIG. 3*a*, through this the illuminated spatial angle can be increased. In FIG. 3*b* it is clear that the light output can in the first instance be increased in that the converging lens 29 is configured as a plano-convex lens which is placed in the beam path in such a way that its planar surface faces the LED 5 and also the distance between the planar surface and LED 5 is minimal, wherein preferably an air gap remains between the two components in order to maintain a sufficiently high refractive index. This makes it possible that even those light rays that leave the LED 5 at a large angle compared to the surface normal, reach the converging lens 29 and are refracted by the latter onto the optical axis. As a result, the light rays can pass through the light filter 25 and the diverging lens 31 and thus reach the object to be illuminated, e.g. the tissue to be examined. The procedure with the plano-convex lens described above, also has the advantage that in comparison with the procedure shown in FIG. 3*a*, the light rays hit the converging lens 29 at smaller angles in relation to the normal and, accordingly, the so-called Fresnel losses are smaller, through which the light output can be increased further. As shown in FIG. 3*c*, the axial length of the particularly strongly curved converging lens 29 can be shortened if it is configured as a Fresnel lens. Even though not shown, the diverging lens 31 can also be configured more thinly as a Fresnel lens.

FIG. 3*d* shows the lens system 19 distally of the first LED 5 in the distal end of the insertion section 1. However, the exact alignment, fitting and fixation of the lens system 19 shown in FIG. 3*d* in the distal end of an insertion section 1 can be very laborious, imprecise and unstable due to the small axial length of the individual components and, in particular, because of the small heights of the respective surfaces that act as interfaces to the recess 11*a*.

Figure 3F:
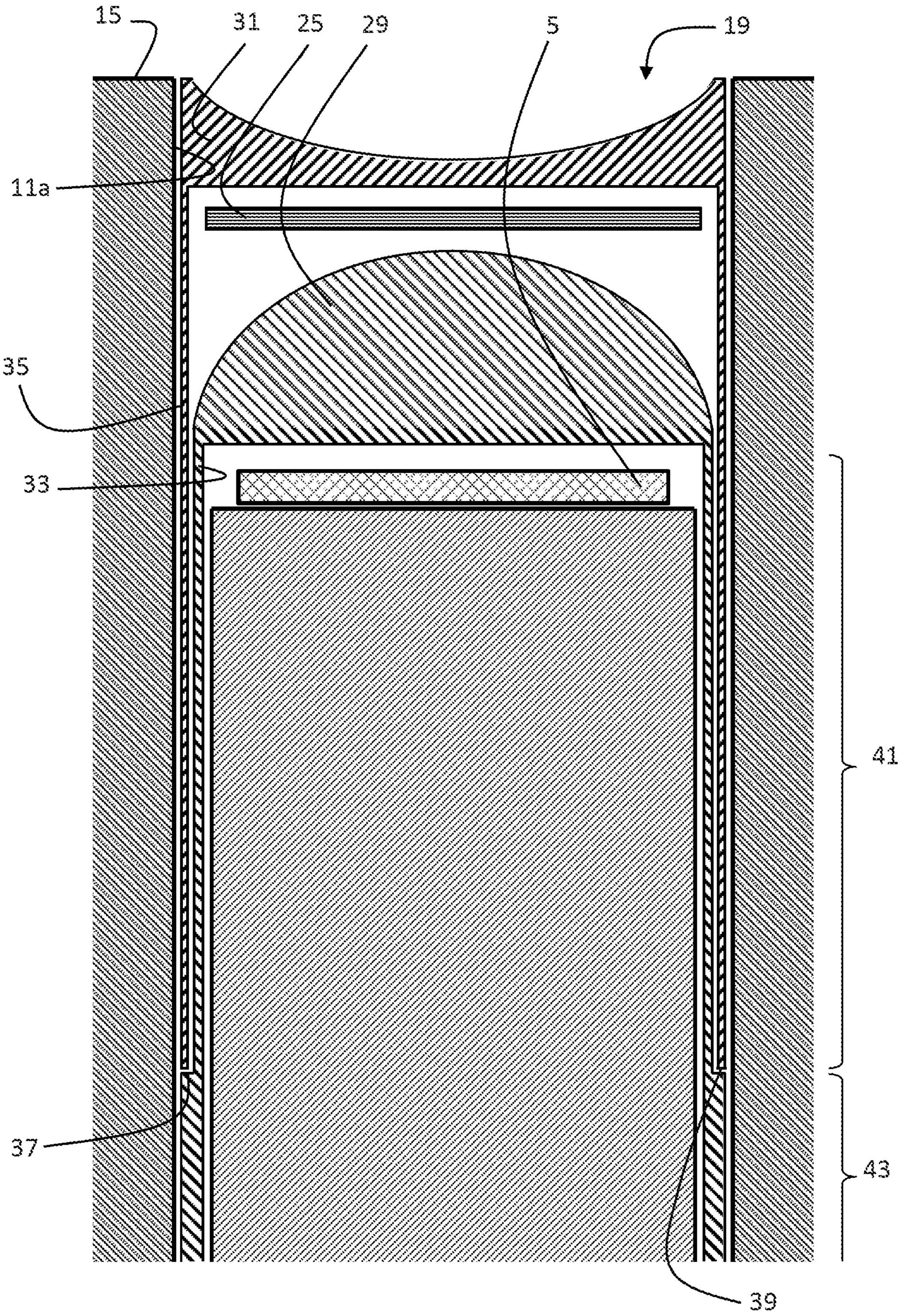

FIGS. 3*e* and 3*f* show particularly advantageous forms of embodiment of the lens system 19 in which both the converging lens 29 comprises a sleeve extension 33 and the diverging lens 31 a sleeve extension 35. The sleeve extensions 33, 35 are thus an integral component of the respective lens 29, 31 configured in one piece. The sleeve extensions 33, 35 are preferably produced by removing a core of a blank by means of an ablative process, for example selective laser etching (SLE). Alternatively, the sleeve extensions 33, 35 with the appurtenant actual lenses 29, 31 can also be produced by additive processes or by combined additive and ablative processes. The sleeve extensions 33, 35 form an outer reference surface with the aid of which the respective lens 29, 31 can be positioned and fixed in the distal end of an insertion section 1 in a much quicker, more stable, simple and precise manner. The sleeve extension 33, 35 extends longer by a factor of 2 or more in the axial direction than the axial thickness of the respective lens on the optical axis.

The light filter 25, which is arranged as close as possible to the planar proximal side of the diverging lens 35, is circumferentially surrounded by the sleeve extension 35 of the diverging lens 31. The converging lens 29 also projects with its curved distal side into the sleeve extension 35 of the diverging lens 31. The first LED 5 is in turn, circumferentially surrounded by the sleeve extension 33 of the converging lens 29. The converging lens 29 forms a distally acting abutment 37 against which a proximal end 39 of the sleeve extension 35 of the diverging lens 31 is supported. Through this, the lenses 29, 31 are aligned precisely coaxially with regard to the optical axis and can be easily, rapidly and securely fitted.

Shown in FIG. 3*f* is a form of embodiment in which the sleeve extension 35 of the diverging lens 31 at least partially surrounds the converging lens 29 and preferably also a distal section 41 of the sleeve extension 33 of the converging lens 29. Here, the abutment 37 is arranged further to proximal than the planar side of the converging lens 29. The first distal section 41 of the sleeve extension 33 of the converging lens 29 has a smaller outer diameter than a second proximal section 43 of the sleeve extension 33 of the converging lens 29. The outer diameter of the first distal section 41 of the sleeve extension 33 of the converging lens 29 fits into the inner diameter of the sleeve extension 35 of the diverging lens 31. The outer diameter of the second distal section 43 of the sleeve extension 33 of the converging lens 29 approximately corresponds to the outer diameter of the sleeve extension 35 of the diverging lens 31. The distally acting abutment 37 of the converging lens is preferably formed by a circumferential ledge between the first 41 and the second section 43 of the sleeve extension 33 of the converging lens 29. The form of embodiment of the "converging lens-light filter-diverging lens" arrangement shown in FIG. 3*f* has the advantage that the components of the "converging lens-light filter-diverging lens" arrangement have relatively large reference surfaces in relation to one another which allow the components to be simply, precisely and stably fixed to each other. As a result of this, the "converging lens-light filter-diverging lens" arrangement can be fitted as a stable pre-assembled unit into a distal end of an insertion section 1 in a rapid, precise and stable manner.

The numbered references to the components or directions of movement as "first", "second", "third" etc. are purely arbitrary in order to distinguish between the components or directions of movement and can be selected in any other way. No order of importance is therefore associated with this. Designating a component or technical feature as "first" should therefore not be misunderstood to the effect that there must be a second component or technical feature of this type. Moreover, any process stages can, unless explicitly explained otherwise or absolutely necessary, be carried out in any sequence and/or partially or fully overlapping in time.

Equivalent forms of embodiment of the parameters, components or functions described herein that in the light of this description appear evident to a person skilled in the art, are covered as if they are explicitly described herein. Accordingly. the protective scope of the claims should cover such equivalent forms of embodiment. "Can" features designated as optional, advantageous, preferably, desired or similar should be understood as optional and not as limiting the scope of protection The described forms of embodiment should be understood as illustrative examples and do not represent an exhaustive list of possible forms of embodiment. Every feature disclosed in relation to a form of embodiment can be used alone or in combination with one or more other features, regardless of in which form of embodiment the respective features have been described. Whereas at least one example of embodiment is described and shown herein, derivations and alternative forms of embodiment that appear evident to a person skilled in the art on the basis of this description, are covered by the protective scope of this disclosure. Otherwise, neither should the term "comprise" exclude other features of process steps, nor should "one" rule out a plurality. While specific embodiments of the invention have been shown and described in detail to illustrate the application of the principles of the invention, it will be understood that the invention may be embodied otherwise without departing from such principles.

LIST OF REFERENCE NUMBERS

1 Insertion section
3 End face

5 First LED
7 Second LED
9 Image sensor
11*a,b,c* Recess
13 Face wall
15 Outer surface
17*a,b,c* Protective element
19 Lens system
21 Objective lens
23 Longpass filter
25 Shortpass filter
27 Transmission spectrum of the shortpass filter
29 Converging lens
31 Diverging lens
33 Sleeve extension of the converging lens
35 Sleeve extension of the diverging lens
37 Abutment
39 Proximal end of the sleeve extension of the diverging lens
41 Distal first section of the sleeve extension der converging lens
43 Distal second section of the sleeve extension der converging lens

The invention claimed is:

1. A medical endoscopic instrument comprising:

a distal elongated insertion section configured for minimally invasive insertion into a human or animal body;

a LED arranged in a distal end section of the insertion section;

a lens system arranged distally of the LED, the lens system having an optical axis, wherein the lens system comprises a first lens and a second lens arranged distally of the first lens, and wherein the second lens includes a proximally extending sleeve extension and wherein the first lens includes a sleeve extension with a distal section and a proximal section, wherein the sleeve extension of the second lens includes a first reference surface for positioning the second lens in relation to the insertion section and a second reference surface for positioning the first lens in relation to the second lens, wherein the second lens is a plano-concave lens with a planar surface, the planar surface of the second lens facing in a proximal direction; and a shortpass filter being arranged at the planar surface of the second lens, wherein the sleeve extension of the second lens surrounds the shortpass filter, the first lens, the LED and the distal section of the sleeve extension of the first lens.

2. The medical endoscopic instrument according to claim 1, wherein the sleeve extension of the second lens is configured in one-piece with the second lens as an integral part of the second lens, the second lens being located at a first distance from an end of an end section of the insertion section, the first lens being located at a second distance from the end of the end section of the insertion section, the first distance being less than the second distance.

3. The medical endoscopic instrument according to claim 1, wherein the sleeve extension of the second lens extends longer, by a factor of 2 or more in an axial direction, than an axial thickness of the second lens on the optical axis, the shortpass filter being arranged between the first lens and the second lens.

4. The medical endoscopic instrument according to claim 1, wherein the first lens forms a distally acting abutment which is axially supported against the second reference surface of the sleeve extension of the second lens.

5. The medical endoscopic instrument according to claim 1, wherein the LED is circumferentially surrounded by the sleeve extension of the first lens.

6. The medical endoscopic instrument according to claim 1, wherein the sleeve extension of the second lens is produced by removing a core of a blank by means of an ablative process.

7. The medical endoscopic instrument according to claim 1, wherein the sleeve extension of the second lens is produced by means of an additive process.

8. The medical endoscopic instrument according to claim 1, wherein the sleeve extension of the second lens is produced by a combined additive and ablative process.

9. The medical endoscopic instrument according to claim 1, wherein the first lens is a converging lens and the second lens is a diverging lens.

10. The medical endoscopic instrument according to claim 1, wherein the shortpass filter is arranged between the first lens and the second lens.

11. The medical endoscopic instrument according to claim 1, wherein the first lens is a plano-convex lens.

12. The medical endoscopic instrument according to claim 1, wherein the first lens is planar towards the LED.

13. The medical endoscopic instrument according to claim 1, wherein the first lens and/or the second lens is/are a Fresnel lens.

14. The medical endoscopic instrument according to claim 1, wherein the proximal section of the sleeve extension of the first lens comprises an abutment, the abutment comprising an abutment surface, the sleeve extension of the second lens comprising an end portion, the end portion comprising an end surface, the abutment surface facing in a direction of the end surface.

15. A method of producing a lens system, which is suitable for use in a distal end of a medical endoscopic instrument and comprises at least one lens, wherein a sleeve extension of the at least one lens is created by removing a core of a blank by means of an ablative process, the medical endoscopic instrument comprising a shortpass filter and a distal elongated insertion section, wherein the lens system further comprises another lens arranged distally of the at least one lens, the another lens including a proximally extending sleeve extension and wherein the sleeve extension of the at least one lens includes a distal section and a proximal section, wherein the proximally extending sleeve extension includes a first reference surface for positioning the another lens in relation to the insertion section and a second reference surface for positioning the at least one lens in relation to the another lens, wherein the another lens is a plano-concave lens with a planar surface, the planar surface of the another lens facing in a proximal direction, the shortpass filter being arranged at the planar surface of the another lens, wherein the sleeve extension of the another lens surrounds the shortpass filter, the at least one lens, an LED and the distal section of the sleeve extension of the at least one lens.

16. A method of producing a lens system, which is suitable for use in a distal end of a medical endoscopic instrument, with at least one lens and a sleeve extension, wherein in a first additive step, quartz glass particles are mixed with a certain quantity of liquid plastic and, by way of stereolithography, are hardened by means of light at desired points, and a core of a blank in a form of material that had remained liquid, is then washed out in a solvent bath in a second ablative step so only a desired, hardened structure is left as the at least one lens with the sleeve extension, the medical endoscopic instrument comprising a shortpass filter and a distal elongated insertion section, wherein the lens system further comprises another lens arranged distally of the at least one lens, the another lens including a proximally extending sleeve extension and wherein the sleeve extension of the at least one lens includes a distal section and a proximal section, wherein the proximally extending sleeve extension includes a first reference surface for positioning the another lens in relation to the insertion section and a second reference surface for positioning the at least one lens in relation to the another lens, wherein the another lens is a plano-concave lens with a planar surface, the planar surface of the another lens facing in a proximal direction, the shortpass filter being arranged at the planar surface of the another lens, wherein the sleeve extension of the another lens surrounds the shortpass filter, the at least one lens, an LED and the distal section of the sleeve extension of the at least one lens.

17. The method according to claim 16, wherein the liquid plastic still mixed into the desired, hardened structure is removed by heating.

18. The method according to claim 16, wherein through a final sintering process, the desired, hardened structure is heated to such an extent that the glass particles melt and fuse together.

19. The method according to claim 16, wherein, through removal of the core of the blank, the at least one lens acquires a pot-shaped form which has an optically effective pot base and a mechanically effective circumferential pot wall.

20. The method according to claim 19, wherein an inner surface of the pot base can be ablated in a planar manner.

21. The method according to claim 20, wherein a light filter is attached to the inner surface of the pot base.

22. The method according to claim 19, wherein an outer surface of the pot base can be ablated in an arched manner.

23. The method according to claim 16, wherein the proximally extending sleeve extension of the another lens of the lens system is produced by removing a core of a blank by means of an ablative process.

24. The method according to claim 23, wherein the at least one lens and the another lens are arranged coaxially with regard to each other and at least partially in axial direction fastened to each other in an interlocking manner as the lens system, and the lens system is fitted into the distal end of the medical endoscopic instrument.

* * * * *